(12) United States Patent
DeFilippis

(10) Patent No.: US 6,824,900 B2
(45) Date of Patent: Nov. 30, 2004

(54) METHOD AND APPARATUS FOR WATER MANAGEMENT OF A FUEL CELL SYSTEM

(75) Inventor: Michael S. DeFilippis, Niskayuna, NY (US)

(73) Assignee: MTI MicroFuel Cells Inc., Albany, NY (US)

(*) Notice: Subject to any disclaimer, the term of this patent is extended or adjusted under 35 U.S.C. 154(b) by 165 days.

(21) Appl. No.: 10/090,336

(22) Filed: Mar. 4, 2002

(65) Prior Publication Data

US 2003/0165720 A1 Sep. 4, 2003

(51) Int. Cl.⁷ .............................. H01M 8/04; H01M 8/10
(52) U.S. Cl. ............................ 429/13; 429/30; 429/33; 429/34
(58) Field of Search ............................ 429/13, 30–34, 429/42

(56) References Cited

U.S. PATENT DOCUMENTS

| | | |
|---|---|---|
| 4,420,544 A | 12/1983 | Lawson et al. |
| 5,563,109 A * | 10/1996 | Risse ....................... 429/42 X |
| 5,573,866 A | 11/1996 | Van Dine et al. |
| 5,595,834 A | 1/1997 | Wilson et al. |
| 5,599,638 A | 2/1997 | Surampudi et al. |
| 5,700,595 A | 12/1997 | Reiser |
| 5,773,162 A | 6/1998 | Surampudi et al. |
| 5,795,496 A | 8/1998 | Yen et al. |
| 5,945,231 A | 8/1999 | Narayanan et al. |
| 5,981,097 A | 11/1999 | Rajendran |
| 5,992,008 A | 11/1999 | Kindler |
| 6,007,933 A | 12/1999 | Jones |
| 6,093,501 A | 7/2000 | Werth |
| 6,207,312 B1 | 3/2001 | Wynne et al. |
| 6,248,476 B1 * | 6/2001 | Sun et al. .................. 429/34 X |
| 6,326,097 B1 | 12/2001 | Hockaday |
| 6,465,119 B1 * | 10/2002 | Koripella et al. ............. 429/32 |
| 6,632,553 B2 * | 10/2003 | Corey et al. ............... 429/13 X |
| 2002/0076599 A1 | 6/2002 | Neutzler et al. |
| 2003/0031902 A1 | 2/2003 | Balasubramanian et al. |
| 2003/0031913 A1 * | 2/2003 | Pavio et al. .................. 429/34 |
| 2003/0170508 A1 * | 9/2003 | Beckmann et al. ........... 429/13 |

FOREIGN PATENT DOCUMENTS

JP    2001-185181 A    7/2001

* cited by examiner

Primary Examiner—Stephen J. Kalafut
(74) Attorney, Agent, or Firm—Nixon Peabody LLP

(57) ABSTRACT

A method and apparatus for water management in a direct oxidation fuel cell system includes a direct oxidation fuel cell, including: a housing surrounding an anode, a cathode, a protonically conductive electronically non-conductive membrane electrolyte disposed between the anode and the cathode, a current collector, and a gas-permeable liquid-impermeable membrane disposed on a side of the cathode opposite the electrolyte. Excess water accumulation is removed from an area between the membrane electrolyte and the gas-permeable liquid-impermeable membrane by a pressure differential generated, preferably by a pump. The pressure differential draws air to the surface of, into, or through the cathode diffusion layer. The pump can be driven by the electricity generated by the fuel cell.

28 Claims, 4 Drawing Sheets

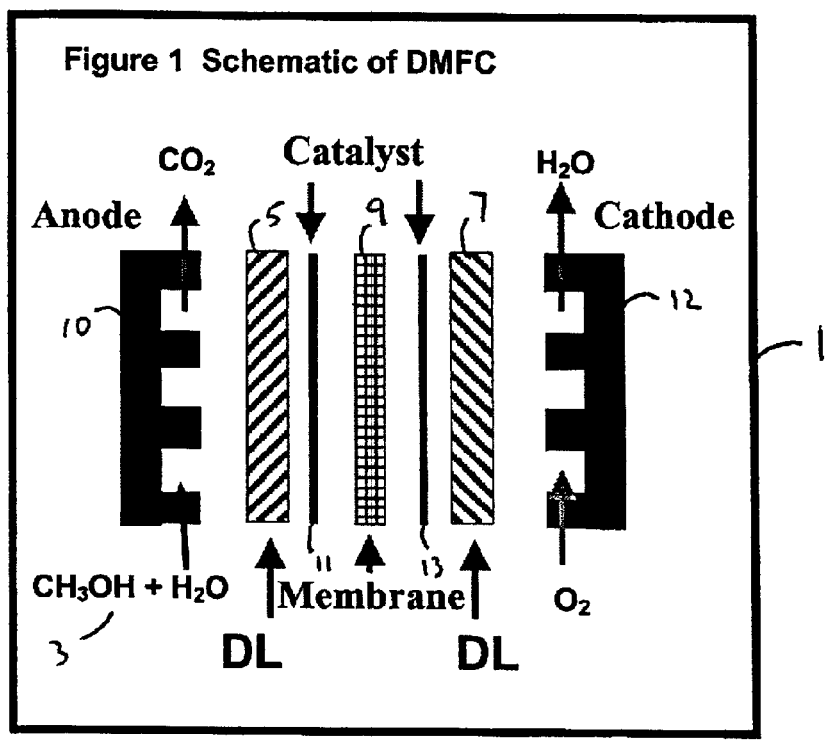

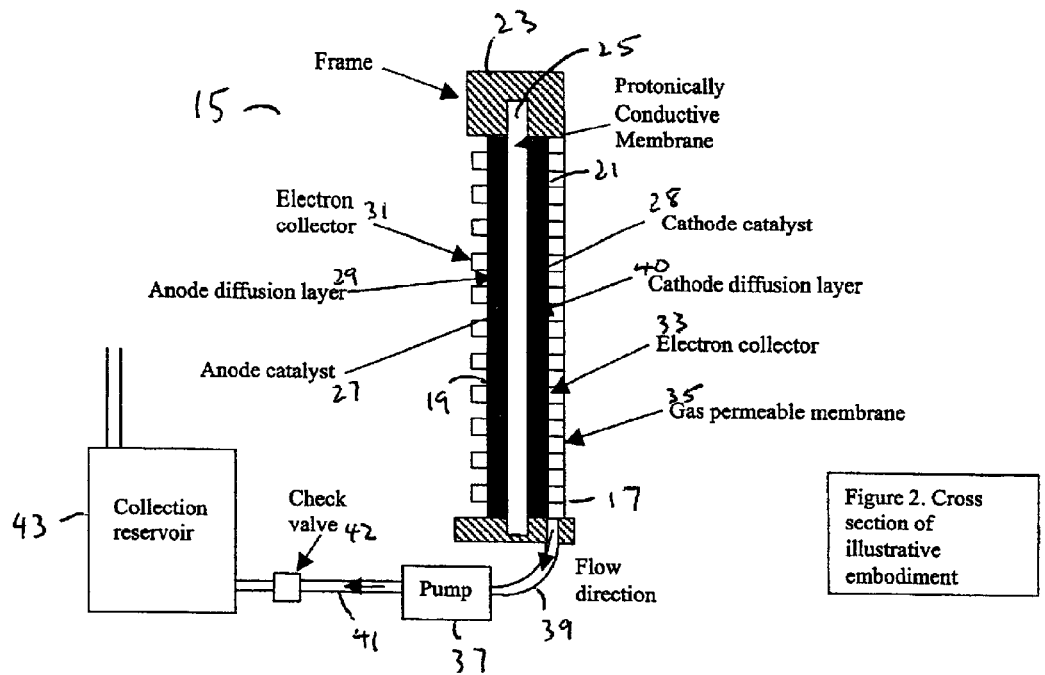
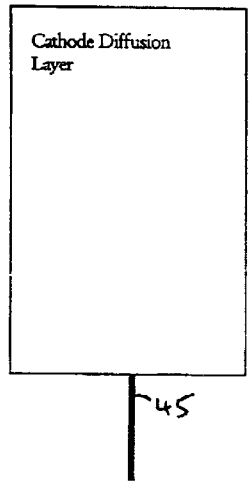
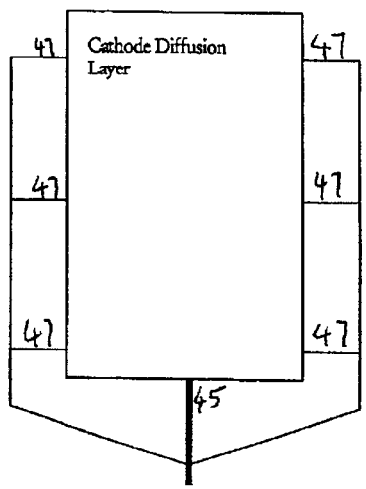
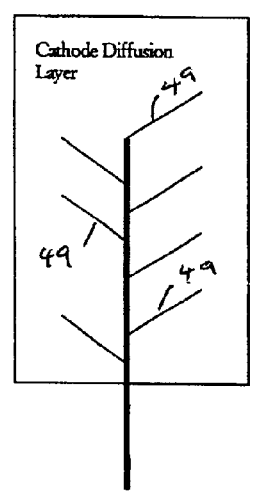
FIGURE 3A       FIGURE 3B       FIGURE 3C

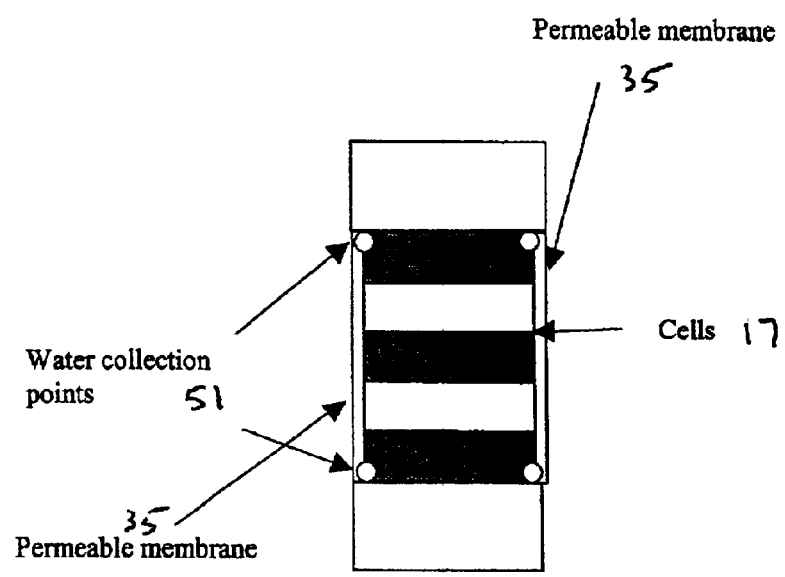
Figure 4: Alternate embodiment for fuel cell stack (cross section)

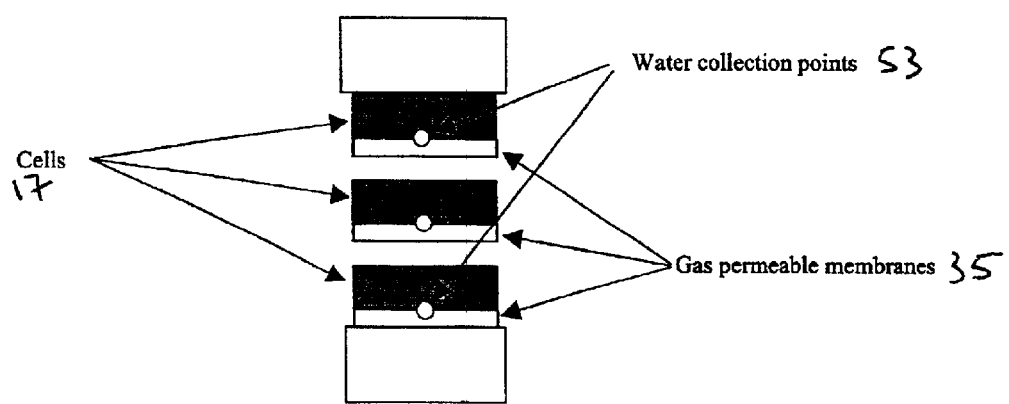
Figure 5: Alternate embodiment for fuel cell stack (cross section)

METHOD AND APPARATUS FOR WATER MANAGEMENT OF A FUEL CELL SYSTEM

BACKGROUND OF THE INVENTION

1. Field of the Invention

The present invention relates generally to the field of direct oxidation fuel cells for producing electrical energy by electrochemical oxidation/reduction of an organic fuel, and in particular to a direct oxidation fuel cell with integrated water management.

2. The Prior Art

Fuel cell technologies present opportunities for the commercial development of long-lasting power sources for portable power and electronics applications. With the trend toward greater portability of a wide array of consumer electronics, some fuel cell technologies offer promising alternative power sources to meet the increased demand for portable power. Fuel cells can potentially replace or favorably compete with the various types of high density batteries presently used in consumer electronics, such as nickel metal-hydride and lithium ion battery systems, as well as relatively inexpensive alkaline batteries. These types of batteries are less than satisfactory power sources for such consumer electronics as laptop computers and cellular phones either due to their low power density, short cycle life, rechargability or cost. In addition, all these types of batteries present environmental safety concerns and costs for proper disposal.

Fuel cell systems are electricity-generating devices that convert chemical energy into useable electrical energy via a simple electrochemical reaction involving a fuel reactant, such as natural gas, methanol, ethanol, or hydrogen, and an oxidizing agent, typically ambient air or oxygen. Fuel cell systems may be divided into "reformer-based" systems, i.e., those in which the fuel is processed in some fashion before it is introduced into the cell, or "direct oxidation" systems, i.e., those in which the fuel is fed directly into the cell without internal processing. Most currently available stationary fuel cells are reformer-based fuel cells. However, fuel processing requirements for such cells limits the applicability of those cells to relatively large systems.

Referring to FIG. 1, a conventional direct oxidation fuel cell 1, wherein the fuel reactant 3 is fed directly into the fuel cell 1 without internal modification or oxidation, is typically constructed of an anode diffusion layer 5, a cathode diffusion layer 7, and an electrolyte 9, such as a protonically conductive electronically non-conductive membrane electrolyte ("PCM"), that is disposed between the anode and cathode diffusion layers. Fuel reactant is introduced into the fuel cell anode and is presented to a catalytic layer 11 intimately in contact with the anode face of the PCM. The anode catalyst layer separates hydrogen from the fuel reactant into protons and electrons as a result of oxidation. Upon the completion of a circuit which electrically connects the anode and cathode of the fuel cell, protons generated by the anodic catalytic reaction pass through the membrane electrolyte to the cathode of fuel cell. Electrons generated by anodic oxidation of fuel molecules cannot pass through the membrane electrolyte, and seek a path through the load which is being powered. The electrons flow away from the anode catalyst, through the anode diffusion layer, and are collected by a current collector 10, pass through a load (not shown), through a current collector 12, through the cathode diffusion layer and to the cathode catalyst layer 13 where the electrons combine with protons and oxygen to form water.

As long as constant supplies of fuel reactant and an oxidizing agent are available to the fuel cell, it can generate electrical energy continuously and maintain a desired power output. Hence, fuel cells can potentially run laptop computers and mobile phones for several days rather than several hours, while reducing or eliminating the hazards and disposal costs associated with high density and alkaline batteries. A further benefit is that a fuel cell runs cleanly producing water and carbon dioxide as by-products of the oxidation/reduction of the fuel reactant. The challenge is to develop fuel cell technology and to engineer direct fuel cell systems to meet the form and operation requirements of small-scale or "micro" fuel cells for portable electronics applications.

Direct methanol fuel cell ("DMFC") systems are often multi-cell "stacks" including a number of single fuel cells joined to form a cell stack to increase the voltage potential to meet specific electrical power requirements. The feasibility of using DMFC systems as alternative power sources for portable electronics applications will depend upon the reduction of the size of the overall system to meet demanding form factors, while satisfying the necessary power requirements for electrical power applications.

In addition, DMFC systems useful for consumer electronics applications will require development and design engineering that will enable methanol fuel cells to self-regulate and passively generate electrical power under relevant operating conditions, including ambient air temperature and humidity with a minimum of active humidity or temperature regulation. Such operating conditions may further require the reduction or elimination of auxiliary equipment and external moving parts typically associated with present DMFC systems, such as external fins for heat dissipation, fans for cooling and external flow pumps for supplying pressurized gas reactants and water for sufficient membrane humidification. In addition, the volume of peripheral mechanisms or systems, such as pumps and reservoirs used to store and supply methanol fuel and gas separators used to remove gases from liquid fuel cell effluents, will need to be reduced or eliminated in DMFC systems for portable power and consumer electronics applications.

At present, prior art DMFC systems typically operate in two basic configurations, a flow-through configuration and a recirculation configuration, as disclosed, for example in U.S. Pat. Nos. 5,992,008, 5,945,231, 5,795,496, 5,773,162, 5,599,638, 5,573,866 and 4,420,544. The flow-through configuration directly feeds methanol as a vapor or a stream of either neat methanol or an aqueous solution of methanol and water into the anode electrode of the fuel cell. Anodic oxidation by-products, specifically carbon dioxide, as well as fuel impurities and unreacted methanol fuel solution are removed from the fuel cell to the ambient environment. The flow-through configuration has the disadvantages of wasting unused fuel, and making it difficult to manage effluent by-products. In addition, the flow-through configuration presents problems with respect to handling the anode effluent discharged from the fuel cell. Peripheral mechanisms or systems are required with the flow-through configuration of DMFC systems to remove and dispose of the anode effluent discharged from the fuel cell. Such mechanism or systems would render flow-through DMFC systems impractical for use in portable electronics applications.

The recirculation configuration of DMFC systems, however, has the advantages of recirculating the anode effluent back into the anode electrode, which conserves unused methanol fuel and contains the anode effluent generated by the electrochemical oxidation/reduction processes.

Prior art DMFC systems with recirculation configurations address the problems of handling anode effluent, conserving unused methanol fuel and providing a means of managing by-products of the reaction. Such features are highly advantageous for use of DMFC systems in portable power supplies and portable consumer electronics. However, recirculation configurations of prior art DMFC systems must incorporate auxiliary or external peripheral equipment in the recirculation loops that occupy volume and add complexity to DMFC systems due to their use of electrical power, thus limiting the net power output of the DMFC system.

In a DMFC, it is necessary to provide sufficient quantities of fuel (a mixture of water and methanol) to the catalyzed anode face of the PCM, and oxygen to the catalyzed cathode face of the PCM. Failure to allow sufficient quantities of the reactants to be introduced to the PCM results in the cessation of the reactions that generate electricity in a fuel cell.

During operation, the cathode diffusion layer may become saturated by water that is generated on the cathode face of the PCM. The saturation of the diffusion layer prevents oxygen from reaching the cathode face of the PCM, and causes the fuel cell's performance to be compromised, or be halted altogether. In addition, particulate airborne contaminants may clog the openings in the structure of the cathode diffusion layer, thus further limiting the performance of the DMFC. U.S. Pat. No. 6,326,097 to Hockaday discloses the use of a disposable diffusion mat that is integrated into the external housing of the fuel cell system and is used to manage temperature and humidity, and also provides some filtering characteristics as well.

Moreover, it is desirable to supply methanol to the catalyzed PCM in an aqueous solution. By doing so, methanol crossover (a process whereby methanol passes through the PCM without contributing to the generation of electricity) is reduced and the overall utility of the cell is enhanced. It is desirable to carry a more concentrated mixture of fuel, rather than a dilute mixture, for the purpose of minimizing the volume of the fuel cartridge or internal reservoir, and therefore the system. However, to ensure that the DMFC will continue generating electricity, sufficient oxygen must be supplied to the cathode, and under certain operating conditions, it may be necessary to provide a method to facilitate the removal of cathodically generated water and any other fluids that may be present on the cathode face of the PCM, or within the cathode diffusion layer of the fuel cell, including but not limited to liquid water that may be present.

Previously disclosed methods of water removal from the cathode diffusion layer of the fuel cell rely on wicking, drying, or absorption to transport or remove cathodically generated water, or are gravity dependent. The effectiveness of these methods varies with the ambient air temperature and humidity, or the orientation of the device and are difficult to control or vary predictably. As such they are less than ideal for use in portable electronics which will be exposed to a wide variety of conditions during use, and which require that they remain operational during periods of rapid change of such conditions.

There remains a need, therefore, for a direct oxidation fuel cell system that optimizes oxygen being provided to the cathode and prevents excess water accumulation on the cathode face of the PCM and the cathode diffusion layer of the fuel cell. Therefore, it would be desirable to provide a method and apparatus for preventing excess water from saturating the cathode diffusion layer and thereby preventing oxygen from reaching the cathode catalyst layer, and preferably recirculating the excess water to adjust the fuel concentration within the fuel cell system, enabling the system to carry a more concentrated fuel source.

SUMMARY OF THE INVENTION

One aspect of the present invention relates to a system including: a direct oxidation fuel cell, which includes a housing surrounding an MEA, a current collector disposed on the outside of the MEA to collect and conduct electrical current to a load, and a gas-permeable liquid-impermeable membrane disposed on a cathode-side outer surface of the current collector, wherein the MEA includes an anode aspect, a cathode aspect, and a PCM disposed between the anode aspect and the cathode aspect; a source of fuel in communication with the anode aspect; a source of oxygen in communication with the cathode aspect, so as to produce electricity-generating reactions, including anodic disassociation of a fuel and water mixture to produce carbon dioxide, protons and electrons and a cathodic combination of protons, electrons and oxygen to produce water; and a pump in fluid communication with an area between the PCM and the gas-permeable liquid-impermeable membrane, connected to remove excess water produced at the cathode aspect.

Another aspect of the present invention relates to a system including a direct oxidation fuel cell, which includes a housing surrounding an MEA, including an anode diffusion layer, a cathode diffusion layer, and a PCM disposed between the anode diffusion layer and the cathode diffusion layer, a catalyst layer is preferably disposed on one or both faces of the PCM in intimate contact with the PCM and the diffusion layer, a current collector disposed on the outside of the MEA to collect and conduct electrical current to a load, and a gas-permeable liquid-impermeable membrane disposed on an outer cathode-side surface of the current collector; a source of fuel in communication with the anode aspect of the MEA; a source of oxygen in communication with the cathode aspect of the MEA, so as to produce electricity-generating reactions, including anodic disassociation of a fuel and water mixture to produce carbon dioxide, protons and electrons and a cathodic combination of protons, electrons and oxygen to produce water; and a pump in fluid communication with an area between the PCM and the gas-permeable liquid-impermeable membrane, connected to remove excess liquid water produced at the cathode.

Another aspect of the present invention is a method for managing water in a direct oxidation fuel cell, including: providing a direct oxidation fuel cell, including: a housing surrounding an MEA, wherein the MEA includes an anode aspect, a cathode aspect and a PCM disposed between the anode aspect and the cathode aspect, a current collector disposed on the outside of the MEA to collect and conduct electrical current to a load, and a gas-permeable liquid-impermeable membrane disposed on a cathode-side outer surface of the current collector; providing fuel to the anode aspect of the fuel cell; providing oxygen to the cathode aspect of the fuel cell; and removing excess water accumulation from an area between the PCM and the gas-permeable liquid-impermeable membrane.

Another aspect of the present invention relates to a method for managing water in a direct oxidation fuel cell, including: providing a direct oxidation fuel cell, including a housing surrounding an MEA, wherein the MEA includes an anode diffusion layer, a cathode diffusion layer, and a PCM disposed between the anode diffusion layer and the cathode diffusion layer, a catalyst layer is preferably disposed on one or both faces of the PCM in intimate contact with the PCM and the diffusion layer, a current collector disposed on the outside of the MEA to collect and conduct electrical current to a load, and a gas-permeable liquid-impermeable membrane disposed on an outer cathode-side surface of the current collector; providing fuel to the anode diffusion layer of the MEA; providing oxygen to the cathode diffusion layer of the MEA; and removing excess water accumulation from an area between the PCM and the gas-permeable liquid-impermeable membrane.

Another aspect of the present invention relates to a method including: providing a direct oxidation fuel cell, including a housing surrounding an MEA; wherein the MEA includes an anode aspect, a cathode aspect and a PCM disposed between the anode aspect and the cathode aspect, a current collector disposed on the outside of the MEA to collect and conduct electrical current to a load, and a gas-permeable liquid-impermeable membrane disposed on a cathode-side outer surface of the MEA; providing fuel to the anode aspect of the current collector; providing oxygen to the cathode aspect of the PCM; and drawing air to the surface of, into or through the cathode diffusion layer, preferably, via the creation of a pressure differential.

Additional features of the invention will be set forth in the detailed description which follows, and in part will be readily apparent to those skilled in the art from the description or recognized by practicing the invention as described in the written description and claims hereof, as well as appended drawings.

It is to be understood that both the foregoing general description and the following detailed description are merely exemplary of the invention, and are intended to provide an overview or framework to understanding the nature and character of the invention as it is claimed.

BRIEF DESCRIPTION OF THE DRAWINGS

The accompanying drawings are included to provide a further understanding of the invention, and are incorporated in and constitute a part of this specification. The drawings illustrate one or more embodiment(s) of the invention, and together with the description serve to explain the principles and operation of the invention. In the drawings, FIG. 1 is a schematic diagram of a prior art DMFC;

FIG. 2 is a cross-section view of the fuel cell system in which the present invention is embodied;

FIGS. 3A–C are side plan views of various embodiments of the cathode diffusion layer;

FIG. 4 is a cross-section view of an alternate embodiment of a fuel cell stack; and FIG. 5 is a cross-section view of an alternate embodiment of a fuel cell stack.

DETAILED DESCRIPTION OF PREFERRED EMBODIMENTS

The present invention provides a method and apparatus for water management for a direct oxidation fuel cell system. More particularly, cathodically generated water is preferably directed to the anode where it can be mixed with fuel from a more concentrated fuel source in order to provide a more dilute fuel mixture. For purposes of illustration, we herein describe an illustrative embodiment of the invention as it is employed in connection with a direct methanol fuel cell system ("DMFC system"), with the fuel substance being methanol or an aqueous methanol solution. It should be understood, however, that it is within the scope of the present invention that the water management apparatus and method can be readily used with other fuels that are compatible with direct oxidation fuel cell systems. Thus, as used herein, the terms "fuel", "fuel reactant", and "fuel mixture" shall include methanol, ethanol, or combinations thereof and aqueous solutions thereof and other carbonaceous fuels that are suitable for use in a direct oxidation fuel cell system.

FIG. 2 shows a direct methanol fuel cell system 15 incorporating the water management apparatus of the present invention. The system is preferably disposed within a casing (not shown) for use in portable applications. In a preferred embodiment, the direct oxidation fuel cell system 15 contains a direct methanol fuel cell 17. The fuel cell has anode chamber 19 and cathode chamber 21 surrounded by a housing 23. The anode chamber and cathode chamber are separated by the PCM 25 which is preferably coated with an anode catalyst 27 and a cathode catalyst 28. A fuel, such as methanol, is supplied to the anode chamber of the DMFC from a fuel source through a pump (not shown), or by using a pressurized cartridge or other fuel delivery system depending on the particular application.

As will be understood by those skilled in the art, an aqueous solution of the carbonaceous fuel (typically aqueous methanol) is presented to a PCM typically through an anode diffusion layer 29, as shown in FIG. 2. The fuel is disassociated by the catalysts in intimate contact with the anode face of the PCM, or which are otherwise present in the anode and cathode chambers, which enable direct oxidation of the carbonaceous fuel on the anode and the reduction of the products of the cathodic reaction on the cathode face of the PCM. Upon the completion of a circuit, the protons pass through the membrane electrolyte which is impermeable to the electrons. The electrons seek a different path to re-unite with the protons and travel through a load and thus provide the electrical power of the cell. This separates the hydrogen protons and electrons from the fuel molecules. The electrochemical reaction equations are as follows:

Anode: $CH_3OH+H_2O=CO_2+6H^++6e^-$  Equation 1

Cathode: $4H^++4e^-+O_2=2H_2O$  Equation 2

Net Process: $CH_3OH+3/2\ O_2=CO_2+2H_2O$  Equation 3

The anodic reaction of the direct oxidation fuel cell, as described in Equation 1, produces carbon dioxide ($CO_2$). A gas separator receives the anode effluent and separates gaseous carbon dioxide from any un-reacted methanol or aqueous methanol solution which may be sent to a pump to be reintroduced to the anode chamber as desired in a particular application. Water is produced in the cathode chamber, by the cathodic reaction described in Equation 2. A second gas separator receives the cathode effluent and separates the cathodic effluent from the cathode into liquid (i.e., water, which may be supplied to a pump) and vapor and air, which may be released into the environment.

Direct methanol fuel cells, such as the fuel systems disclosed in U.S. Pat. Nos. 5,992,008, 5,945,231, 5,773,162, 5,599,638, 5,573,866 and 4,420,544, which are herein incorporated by reference in their entirety, typically employ proton conducting, cation-exchange polymer membranes constructed of a perfluorocarbon sulfonic acid (PFSA) ionomer, such as NAFION® commercially available from E. I. duPont de Nemours and Co. Commercially available NAFION® membranes that act as membrane electrolytes for DMFC systems generally have a thickness of 25 to 175 µm. Composite membranes are also commercially available and can act as membrane electrolytes. Composite membranes are significantly thinner than homogeneous ionomeric membranes and generally have a thickness of 10 to 25 $\mu$m. Such composite membranes include, for instance, a polytetrafluorotheylene (PTFE) micromesh material with PFSA-filled pores available from W.L. Gore, Inc. of Newark, Del.

Preferably, a catalyst layer is in intimate contact with each face of the PCM. The catalytic layers are composed of electrocatalysts that catalyze the electrochemical oxidation and reduction of the fuel reactant, wherein an anode electrocatalyst disassociates hydrogen protons from the fuel reactant and a cathode electrocatalyst effects reduction of hydrogen ions with oxygen to form water. High surface area particles, such as platinum and ruthenium alloy particles, are commonly used as anode electrocatalysts, as disclosed in U.S. Pat. No. 5,523,177, which is herein incorporated by reference in its entirety. However, ternary or quaternary catalyst layers are also possible. A suitable cathode electrocatalyst is platinum-black (Pt-black) which is typically applied to the membrane electrolyte to form an appropriate site for electrochemical reduction. As used herein, the term "catalyst layer" may be used interchangeably with the term "catalyst." The catalyst layer is sometimes referred to as being a part of the PCM, for example, where interfaces between the components of the fuel cell are described.

Preferably, each electrocatalyst layer is in intimate contact with a diffusion layer. The diffusion layer allows the introduction of reactants and removal of by-products of the electrochemical reactions that occur on the catalyzed surface of the PCM, and are generally fabricated from un-catalyzed porous carbon paper or carbon cloth with a layer containing PTFE and high surface area particles. The anode diffusion layer serves to uniformly distribute the fuel mixture to the catalyzed anode face of the PCM, while providing a path by which carbon dioxide may be released. The cathode diffusion layer serves to uniformly distribute the oxidant or air to the catalyzed cathode face of the PCM, while providing a path by which anodically generated water may be removed from the cathode face of the membrane. The cathode diffusion layer provides an effective supply of oxidizing agent, air or oxygen, while removing water or water vapor from the membrane electrolyte formed from electrochemical reduction of hydrogen ions. In addition to providing the introduction of reactants to and removal of the products of the energy producing reaction from the catalyzed faces of the PCM, each diffusion layer conducts electricity generated by the energy producing reactions.

The diffusion layer is typically constructed of a porous carbon fiber paper and/or carbon cloth that is well known in the art including, although not limited to, TORAY® paper or E-TEK® cloth available from E-Tek, Inc., Division of DeNora N.A., Inc. of Sommerset, N.J. Although dependent upon the material of construction, the anode diffusion layer has a thickness generally in the range of about 150 $\mu$m to about 400 $\mu$m. The diffusion layer may be additionally treated with additives well known in the art, which effectively increase diffusion or other properties of the diffusion layer, such as, although not limited to, TEFLON® for wet-proofing, and high surface area carbon particles to enhance electrical conductivity.

The membrane electrode assembly ("MEA") preferably includes an anode diffusion layer, a cathode diffusion layer, and a PCM disposed between the anode diffusion layer and the cathode diffusion layer. A catalyst layer is preferably disposed on one or both faces of the PCM in intimate contact with the respective diffusion layer. Those skilled in the art will recognize that preferably, the PCM, catalyst layers, and diffusion layers are typically placed in intimate contact with, or otherwise bonded with each other and/or bonded to each other to form the MEA. Although the specific construction of the MEA in terms of components and structure may vary, the MEA is defined as a structure which facilitates the introduction of reactants, the maintenance of the electrochemical reactions and the removal of un-reacted reactants and reaction products and by-products to provide an electricity generating fuel cell. As used herein the terms "cathode", "cathode chamber" and "cathode aspect of the MEA" are interchangeable and meant to designate that portion of the fuel cell where the protons, electrons and oxygen are combined to form cathodically generated water. As used herein the terms "anode", "anode chamber" and "anode aspect of the MEA" are interchangeable and meant to designate that portion of the fuel cell where the protons, electrons and carbon dioxide are produced from the anodic disassociation of a fuel and water mixture.

Current collector plates 31 and 33 or other current collecting components may be located on outer sides of the MEA of the fuel cell unit to conduct and collect electrons generated by the electrochemical oxidation of methanol. Suitable collector plates are typically constructed of carbon composites or metals, such as stainless steel and titanium, exhibit high electronic conductivity, and do not corrode or otherwise deteriorate in the presence of methanol, water, oxygen or other reactants or by-products. Collector plates may be configured as bipolar plates and may be shaped to form flow fields having a range of flow channel geometry that provides effective mass transport of reactants, as well as effective removal of by-products of the reaction, including carbon dioxide and water. Alternatively, the current collector may be a thin screen or foil that is in contact with the diffusion layer of the MEA.

In one embodiment of the present invention, the system includes: a direct oxidation fuel cell having a housing surrounding an MEA, a collector in communication with the MEA for capturing and conducting current, and a gas-permeable liquid-impermeable membrane 35 disposed on an outer cathode-side surface of the current collector; a source of fuel and a fuel delivery system that delivers fuel to the anode aspect of the MEA; a source of oxygen, preferably ambient air, in communication with the cathode aspect of the MEA, so as to allow the electricity producing reactions to occur; and an apparatus for creating a pressure differential, such as for example, a small commercially available pump 37, in fluid communication with an area between the PCM and the gas-permeable liquid-impermeable membrane, connected to remove excess liquid water produced at the cathode side of the MEA. Preferably the gas-permeable liquid-impermeable membrane is disposed on the outer surface of the cathode collector. The housing need not entirely, or even substantially surround the MEA, and a portion of the housing may be partially open in order to allow the flow of oxygen and fuel.

The present invention also includes a method for managing water in a direct oxidation fuel cell, including: providing a direct oxidation fuel cell, including a housing surrounding an MEA, a collector in communication with the MEA for capturing and conducting current, and a gas-permeable liquid-impermeable membrane disposed on an outer cathode-side surface of the current collector; providing fuel to the anode aspect of the MEA; providing oxygen to the cathode aspect of the MEA; and removing excess liquid water accumulation from an area between the PCM and the gas-permeable liquid-impermeable membrane.

In a preferred embodiment, a cathode diffusion layer fabricated from typical materials is placed in intimate contact with the PCM, at least one face of which has a catalyst applied to it, using methods well known to those skilled in the art. To the collector disposed on the cathode diffusion layer, a gas-permeable liquid barrier, preferably a membrane such as expanded PTFE, is attached to the face opposite the PCM. (FIG. 2) Alternatively, the barrier could be formed by applying a liquid to the surface of the cathode collector of the MEA, which, when dry, would form a barrier to liquids but not gasses.

The gas-permeable liquid-impermeable membrane prevents liquid water from escaping from the cathode aspect of the MEA, preferably the cathode diffusion layer, and acts as a filter to remove particulate contaminants from the air while at the same time creating a finite volume against which a pressure differential is created, for example, by a pump or other apparatus capable of creating suction. For convenience, an embodiment of the present invention illustrates the use of a pump for creating a pressure differential. However, the invention is not so limited and any apparatus capable of creating a pressure differential sufficient to remove cathodically generated liquid water is suitable for use in the present invention. Moreover, this pressure differential enables a uniform removal of water from, for example, the cathode diffusion layer, allowing increased air access to the cathode aspect of the MEA. The invention further enables the increased introduction of air to the surface of, or the induction of air into or through the cathode aspect of the MEA, preferably the diffusion layer. The pressure differential may be applied to the cathode side between the gas-permeable liquid-impermeable membrane, which is applied to the cathode-side outer surface of the MEA collector, and the PCM, so that cathodically generated water may be removed from the cathode aspect of the MEA, e.g., diffusion layer, to prevent water accumulation and enable sufficient amounts of oxygen to reach the cathode face of the PCM.

As shown in FIG. 2, the pump 37 is connected to the fuel cell by a first conduit 39. One end of the first conduit 39 is connected to an opening in the cathode side of the MEA, which is in communication with the area between the gas-permeable liquid-impermeable membrane and the PCM. The MEA may contain a channel or a plurality of channels within, for example, the cathode diffusion layer 40, for the removal of water, which can be connected to the first conduit. The other end of the first conduit is connected to the inlet of the pump 37. A second conduit 41 is connected to the outlet of the pump and a collection reservoir 43, as shown in FIG. 2. The second conduit 41 may be fabricated from a gas-permeable liquid-impermeable material to remove any residual gasses from the water. In addition, a check valve 42 may be placed between the pump and the collection reservoir in order to prevent the backflow of water into the cathode aspect of the MEA. The collection reservoir is preferably connected to the fuel source, wherein the pump effluent is recirculated to adjust the fuel concentration. Alternately, the second conduit may be connected to vent the excess water to the outside environment. Power can be supplied to the pump through electrical leads (not shown) from an outside source or from the electricity produced by the fuel cell.

The pump may apply suction at one point 45 on or within the cathode diffusion layer, as shown in FIG. 3A. However, when the diffusion layer is sufficiently large, or a smaller pump is desired, it may be beneficial to: 1) collect water from multiple points 47 on or within the diffusion layer (FIG. 3B); 2) form a series of conduits or channels 49 where fluids may flow preferentially that extends throughout the diffusion layer (FIG. 3C); or 3) establish a conduit with multiple collection points perforated into the wall of the tube (not shown). Each of these configurations facilitates a uniform collection of water and a uniform introduction of air allowing improved transport of liquids and oxygen to the cathode diffusion layer leading to enhanced performance of the diffusion layer, and thus of the cathode and fuel cell system as well.

Once water is collected from the cathode, it may be returned to the anode recirculation loop, where it can be used to adjust the concentration of the fuel, or to the anode diffusion layer. Excess water can be eliminated from the system using methods known to those skilled in the art. The gaseous by-products and excess reagents of the electrochemical processes are removed from the fuel cell by one or more vents by methods known to one of ordinary skill in the art. Cathodically generated water may be removed from the system and is preferably recirculated to the fuel source by a pump. In addition, the pump may be used to apply suction to the cathode diffusion layer in order to increase the airflow to the cathode diffusion layer, which will improve the performance of the fuel cell system. This has been shown to be useful where the performance of the fuel cell system is limited by the rate of the cathodic half reaction.

In a further preferred embodiment, in a fuel cell stack composed of an assembly of multiple fuel cells, including those assembled in a "stack" configuration, the gas-permeable liquid-impermeable membrane can be placed on more than one cell in a manner which provides air access to multiple cells of the assembly. Water collection is provided at the corner locations 51 of each gas-permeable liquid-impermeable membrane 35 (FIG. 4), and/or the anode chamber. This embodiment utilizes multiple water outlet channels, and provides a measure of orientation independence with respect to the removal of cathodically generated water. The functionality of this embodiment is suited to situations where gravity causes the water to drain to the proper corners. Because there are water collection points located on different parts of the system, this configuration is particularly useful in situations where the fuel cell system will not remain in a constant orientation during use.

In a further preferred embodiment, wherein a fuel cell stack is composed of multiple cells the gas-permeable liquid-impermeable membrane can be placed on the face of each individual cathode. Water collection is possible at single or multiple points 53 on each cell. Electrical conductivity from cell to cell could be achieved by either selectively connecting cells by piercing the gas-permeable liquid-impermeable membrane 35 or connecting around the gas-permeable liquid-impermeable membrane 35. (FIG. 5).

The water management system of the present invention is also suitable for use in a DMFC system equipped with an anode recirculation configuration. The advantages of recirculating the anode effluent back into the anode electrode, includes conserving unused methanol fuel and containing the anode effluent generated by the electrochemical oxidation/reduction processes. A DMFC system that operates in an anode recirculation configuration includes an external fuel source and a delivery mechanism to supply the anode electrode of the fuel cell with methanol, typically as a methanol and water solution, and an external air source to supply the cathode electrode with air, as an oxidizing agent. The anode effluent contains by-products of the anodic oxidation of methanol, including carbon dioxide and un-reacted methanol, while the cathode effluent contains by-products of the cathodic combination of hydrogen ions and oxygen, as well as the product of the catalytic oxidation of any methanol that has crossed through the PCM without contributing to the reaction, including water vapor, liquid water and air. Gas separators incorporated in effluent return lines are used to remove gases from effluent fluids. The gas separator incorporated in an anode effluent return line effectively separates carbon dioxide from the unused methanol solution and exhausts carbon dioxide from the DMFC system. Similarly, the gas separator incorporated in the cathode effluent return line separates gasses from liquids, allowing water to be returned to the fuel delivery mechanism.

The operating conditions may be monitored using sensors and measuring devices. Operating conditions, such as pressure, temperature, humidity and the like may be measured to determine whether to increase or decrease the flow of water from the cathode chamber, under particular circumstances.

It should be understood that the pump need not be placed directly contiguous to the cathode chamber, but may be placed in a different location that provides the proper removal of excess water. It is possible, for example, that additional channels may be placed at different locations within the fuel cell and configured to drain water from the cathode chamber. In addition, it may be desirable to configure more than one pump, for example to maintain efficient water removal as desired. Alternatively, it may be possible to use a single pump for multiple functions within the fuel cell system.

The invention is readily adaptable to a number of pump designs depending on the application with which the direct oxidation fuel cell power system is being employed. For example, the pumps may be selected from a number of designs known to those skilled in the art, including but not limited to a piezoelectrically driven pump, a mechanical pump, or an electro-osmotic pump, and may be fabricated using conventional techniques.

It should be understood that the present invention provides a method and apparatus to facilitate the removal of excess water from the cathode of a direct oxidation fuel cell. The water generated as a by-product of the reactions in the fuel cell can be recirculated to adjust the fuel concentration. A 50% aqueous solution of methanol is a preferred fuel. This allows for increased efficiency of the fuel carrying capacity of the fuel cell while recycling the water which is generated in the reaction. A number of embodiments of the invention have been described and the embodiment best suited to a particular application can be selected for adaptation in that application.

The foregoing description has been directed to specific embodiments of the invention. It will be apparent, however, that other variations and other modifications may be made to the described embodiments, with the attainment of some or all of the advantages of such, therefore, it is the object of the appended claims to cover all such variations and modifications as come within the true spirit and scope of the invention.

What is claimed is:

1. A system comprising:
   a direct oxidation fuel cell, comprising a housing surrounding an MEA, a current collector disposed on the outside of the MEA to collect and conduct electrical current to a load, and a gas-permeable liquid-impermeable membrane disposed on a cathode-side outer surface of the current collector, wherein said MEA comprises an anode aspect, a cathode aspect, and a PCM disposed between the anode aspect and the cathode aspect;

a source of fuel in communication with the anode aspect;
   a source of oxygen in communication with the cathode aspect, so as to produce electricity-generating reactions, comprising anodic disassociation of a fuel and water mixture to produce carbon dioxide, protons and electrons and a cathodic combination of protons, electrons and oxygen to produce water; and
   a pump in fluid communication with an area between the PCM and the gas-permeable liquid-impermeable membrane, connected to remove excess water produced at the cathode aspect.

2. The system of claim 1, wherein said pump is in fluid communication with the fuel source and connected to pump water produced at the cathode side to the fuel source to adjust the fuel concentration to the desired level.

3. The system of claim 1, wherein said pump is driven by the electricity generated by the fuel cell.

4. The system of claim 1, wherein said current collector comprises a wire mesh.

5. The system of claim 1, wherein said PCM includes a cathode catalyst layer which comprises platinum.

6. The system of claim 1, wherein said PCM includes an anode catalyst layer which comprises a platinum/ruthenium alloy or platinum.

7. The system of claim 1, wherein said MEA comprises at least one conduit in communication with said pump.

8. The system of claim 1, wherein said PCM comprises a perfluorocarbon sulfonic acid ionomer.

9. The system of claim 1, wherein said fuel is organic.

10. The system of claim 9, wherein said fuel is an aqueous solution of methanol.

11. The system of claim 10, wherein said fuel is about 50% aqueous solution of methanol.

12. The system of claim 1, wherein said pump is connected to said MEA by a conduit.

13. A method for managing water in a direct oxidation fuel cell, comprising:
    providing a direct oxidation fuel cell, comprising: a housing surrounding an MEA, a current collector disposed on the outside of the MEA to collect and conduct electrical current to a load, and a gas-permeable liquid-impermeable membrane disposed on a cathode-side outer surface of the current collector, wherein said MEA comprises an anode aspect, a cathode aspect and a PCM disposed between the anode aspect and the cathode aspect;
    providing fuel to the anode aspect of the fuel cell;
    providing oxygen to the cathode aspect of the fuel cell; and removing excess water accumulation from an area between the PCM and the gas-permeable liquid-impermeable membrane.

14. The method of claim 13, wherein said excess water is removed by a pressure differential created in the area between the PCM and the gas-permeable liquid-impermeable membrane.

15. The method of claim 14, wherein said pressure differential is created by a pump.

16. The method of claim 15, wherein said pump is a piezoelectically driven pump, a mechanical pump, or an electro-osmotic pump.

17. The method of claim 13, further comprising recirculating at least a portion of the removed water to adjust the fuel concentration.

18. The method of claim 13, wherein said excess water is recirculated by a pump in fluid communication with the fuel source and the area between the PCM and the gas-permeable liquid-impermeable membrane to adjust the fuel concentration to a desired level.

19. The method of claim 13, wherein said gas-permeable liquid-impermeable membrane filters the oxygen provided to the cathode aspect.

20. The method of claim 15 or 18, wherein said pump is driven by the electricity generated by the fuel cell.

21. The method of claim 13, wherein said fuel is organic.

22. The method of claim 21, wherein said fuel is an aqueous solution of methanol.

23. A method of operating a direct oxidation fuel cell, comprising:

providing a direct oxidation fuel cell, comprising: a housing surrounding an MEA, a current collector disposed on the outside of the MEA to collect and conduct electrical current to a load, and a gas-permeable liquid-impermeable membrane disposed on a cathode-side outer surface of the current collector, wherein said MEA comprises an anode aspect, a cathode aspect and a PCM disposed between the anode aspect and the cathode aspect;

providing fuel to the anode aspect of the fuel cell;

providing oxygen to the cathode aspect of the fuel cell; and drawing air to the surface of, into or through the cathode aspect of the MEA.

24. The method of claim 23, wherein said air is drawn through the MEA by a pressure differential created in the area between the PCM and the gas-permeable liquid-impermeable membrane.

25. The method of claim 24, wherein said pressure differential is created by a pump.

26. The method of claim 25, wherein said pump is a piezoelectically driven pump, a mechanical pump, or an electro-osmotic pump.

27. The method of claim 23, wherein said gas-permeable liquid-impermeable membrane filters the oxygen provided to the cathode.

28. The method of claim 25, wherein said pump is driven by the electricity generated by the fuel cell.

* * * * *